United States Patent [19]

Robicsek et al.

[11] Patent Number: 4,827,906
[45] Date of Patent: May 9, 1989

[54] APPARATUS AND METHOD FOR ACTIVATING A PUMP IN RESPONSE TO OPTICAL SIGNALS FROM A PACEMAKER

[75] Inventors: Francis Robicsek, Charlotte, N.C.; Richard P. Morency, Rock Hill, S.C.

[73] Assignee: Heineman Medical Research Center, Charlotte, N.C. ; A part interest

[21] Appl. No.: 175,612

[22] Filed: Mar. 24, 1988

Related U.S. Application Data

[63] Continuation of Ser. No. 91,270, Aug. 31, 1987, abandoned.

[51] Int. Cl.⁴ .............................................. H61M 1/60
[52] U.S. Cl. ...................................... 600/17; 623/3
[58] Field of Search ................... 128/1 D, 344, 419 P, 128/214, DIG. 3; 3/1

[56] References Cited

U.S. PATENT DOCUMENTS

| | | | |
|---|---|---|---|
| 3,791,374 | 2/1974 | Guarino | 128/1 D |
| 3,860,968 | 1/1975 | Shapiro | 3/1 |
| 4,014,317 | 3/1977 | Bruno | 128/1 D |
| 4,080,958 | 3/1978 | Bregman et al. | 128/1 D |
| 4,541,417 | 9/1985 | Krikorian | 128/1 D |
| 4,583,525 | 4/1986 | Suzuki et al. | 128/1 D |
| 4,627,419 | 12/1986 | Hills | 128/1 D |
| 4,644,936 | 2/1987 | Schiff | 128/1 D |

*Primary Examiner*—Edward M. Coven
*Attorney, Agent, or Firm*—Shefte, Pinckney & Sawyer

[57] ABSTRACT

A method and apparatus for activating a pulsatile heart-lung bypass pump, intra-aortic balloon pump or the like on a patient whose heart is externally paced by a pacemaker of the type having a surface with an optical indicating device which emits optical signals corresponding to pacer signals generated by the pacemaker. The method comprises the steps of optically sensing the optical signals, converting the optical signals sensed into electrical signals phased with the pacer signals generated by the pacemaker, and activating the pump in response to the electrical signals for operation of the pump in phase with the pacer signals. The apparatus accomplishes the steps of the method by use of optical coupling transistors within a bracket adapted for disposition in covering facing relation with the surface of the pacemaker for sensing by the transistors of optical signals emitted by the optical indicating device, the transistors convert the optical signal to electrical signals, and an activating circuit electrically shapes the waveforms of the electrical signals to simulate ECG signals that are applied to activate the pump.

30 Claims, 4 Drawing Sheets

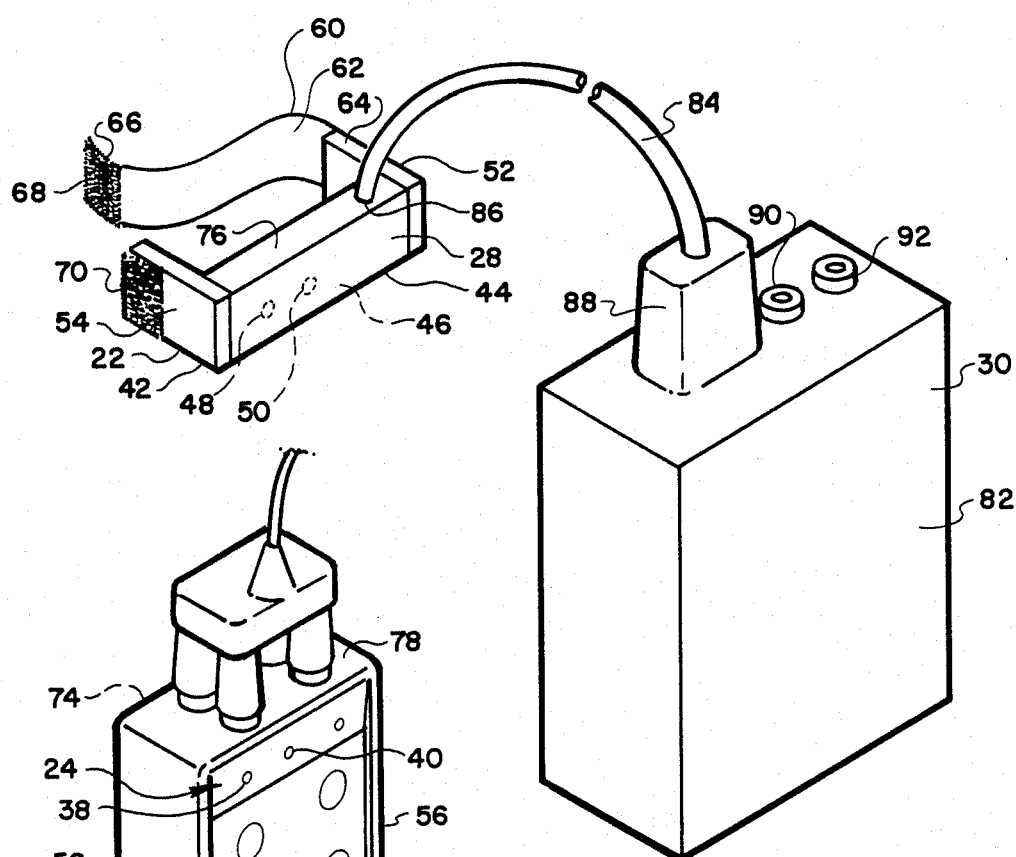
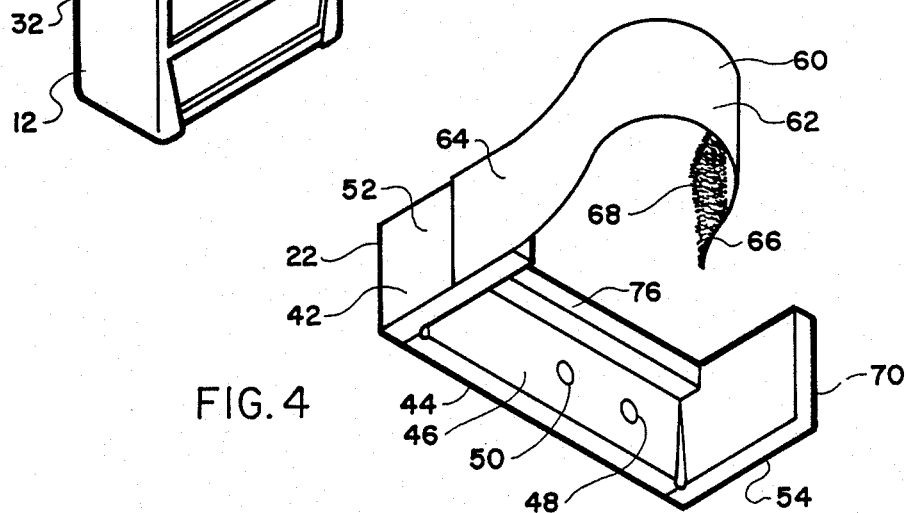
FIG. 3
FIG. 4

APPARATUS AND METHOD FOR ACTIVATING A PUMP IN RESPONSE TO OPTICAL SIGNALS FROM A PACEMAKER

This is a continuation of co-pending application Ser. No. 091,270 field on Aug. 31, 1987, abandoned.

BACKGROUND OF THE INVENTION

The present invention relates to activating a pulsatile heart-lung bypass pump or an intra-aortic balloon pump on a patient whose heart is externally paced, and more particularly to a device for detecting optical signals emitted by the atrial or ventricular pace lights of a pacemaker and electronically converting those optical signals into electrical signals capable of activating the bypass pump or balloon pump.

Often it is necessary during surgery, particularly heart surgery, and during recovery from surgery to provide circulatory support for a weak or failing heart. This support can be provided by a bypass pump, preferably a pulsatile pump activated by an external pulse, or an intra-aortic balloon pump which is activated to deliver a counterpulse.

The success of the intra-aortic balloon pump counterpulsation technique largely depends upon the properly timed activation of the pump to deliver the counterpulse during the ventricular diastole portion of the cardiac cycle. Conventional methods of timing the counterpulsation include activating the pump in response to the atrial or ventricular waveforms of the patient's ECG trace or by application of the arterial pressure curve as a triggering-signal for counterpulsation. All of these signaling methods have disadvantages which can render counterpulsation ineffective when most needed by the patient.

When an atrial spike is present, the pump console will often recognize the atrial spike as well as the QRS complex of the ECG trace and may inflate the balloon twice instead of once during each cardiac cycle, making the assist-process ineffective. Combined application of atrial and ventricular pacing further complicates the matter by further increasing the number of electrical complexes which may trigger the pump. Additionally, inadvertent movement of skin electrodes under the surgical drapes or application of additional electrical devices in the operating room, such as electrocoagulation, can also severely disturb counterpulsation-circulatory assist during the period when it is needed the most by introducing noise and false signals into the counterpulsation triggering circuitry. Changes in the electronic circuitry of newer assist devices, such as the 950-ESIS modification of the KONTRON Model 10 pump marketed by Kontron Corp. of Everett, Massachusetts, altering the position of the sensor electrodes and bipolar atrial electrodes decreases, but does not fully eliminate these difficulties.

Recent application of the arterial pressure curve as the trigger-signal for counterpulsation excludes some of these false signals generated by the paced QRS complex or by an ECG tracing disturbed by other electric interference. This approach, however, has also several shortcomings. First, flattening of the arterial pressure curve due to hypotension or mechanical inadequacy of the pressure-sensing mechanisms, such as a clot or air in the line, makes sensing a trigger-signal impossible. Sensing a trigger-signal from the arterial pressure curve of patients who are being counterpulsated by either balloon-pumps or by specially designed heart-lung machines while being weaned off cardiopulmonary bypass is also extremely difficult. Because a portion of their cardiac output is still diverted through the extracorporeal circuit, their spontaneously generated pulse pressure may be very low and the electric signal generated will not provide an adequate trigger for counterpulsation. This problem receives further impetus by the increase in the application of partial cardiopulmonary bypass using various "non-traumatic" pumps. Also, the arterial pressure curve as the trigger for counterpulsation is often even more vulnerable to mechanical, electrical and electronic interference or noise, especially to electrocoagulation, than the ECG signal.

A pulsatile bypass pump similarly requires well timed activation in phase with the pumping of the patient's heart and is susceptible to the same problems associated with triggering a balloon pump.

The objective of the present invention is to minimize these serious problems in the management of critically ill heart patients.

SUMMARY OF THE INVENTION

The present invention provides a method and apparatus for activating a pulsatile heart-lung bypass pump, intra-aortic balloon pump, or the like on a patient whose heart is externally paced by a pacemaker of the type having an optical indicating means which emit optical signals in response to atrial and ventricular pacer signals being generated by the pacemaker.

Briefly described, the method of the present invention comprises the steps of optically sensing the optical signals, converting the optical signals sensed into electrical signals which are in phase with the pacer signals, and activating the bypass pump or balloon pump in phase with the pacer signals. The present invention also provides an apparatus comprising means for accomplishing the steps of the method.

The pacemaker which is electrically connected directly to the patient's heart includes a low voltage battery power source within safe voltage limits for heart patients while the bypass pump or balloom pump is usually powered by 120 volts A.C. line voltage which presents a potential shock hazard to the patient. Prevailing safety requirements necessitate that the sensing, converting, and activating steps of the present invention be accomplished electrically separate from the pacemaker, that is, without any direct electrical connection between the pacemaker and the pump so that the patient is isolated from possible shock hazard due to shorting of the higher line voltage through the pacemaker.

The shock hazard is eliminated with the present invention by optically sensing the optical signals corresponding to the atrial pacer signals generated by the pacemaker or by optically sensing the optical signals corresponding to the ventricular pacer signals generated by the pacemaker. These optical signals are then converted to electrical signals for activating the pump in response to one of the sensed optical signals.

Converting includes energizing an electrical circuit in response to the optical signal sensing and generating voltage signals at the output of the circuit capable of activating the pump. Preferably, converting includes energizing an atrial converting circuit in response to the optical signals corresponding to the atrial pacer signals and energizing a ventricular converting circuit in response to the optical signals corresponding to the ventricular pacer signals. The converting circuits generate voltage signals at their outputs, and activating involves applying the output voltage signals of one of the circuits to the pump.

In the preferred embodiment of the present invention, activating includes electrically shaping the waveforms of the voltage signals to simulate ECG signals which are capable of activating the pump. Preferably, the electrical shaping of the waveforms of the voltage signals includes simulating an atrial pulse in response to the atrial pacer signal and simulating an R-wave pulse in response to the ventricular pacer signal.

The method of the preferred embodiment of the present invention also includes electrically filtering noise and interference from the electrical signals prior to activating the pump to reduce false activation of the pump.

The present invention also provides an apparatus comprising means of optically sensing the optical signals, means for converting the optically sensed signals into electrical signals, and means for activating the pump in response to the electrical signals for operation of the pump in phase with the pacer signals.

The apparatus of the present invention includes means for electrically shaping the waveforms of the voltage signals of the outputs of the converting circuits. Preferably, the means for electrically shaping the waveforms includes a resistor network configured as a voltage divider with capacitance shunting the divider to simulate an atrial pulse at the output of the activating means in response to the atrial pacer signal and a second voltage divider resistor network with shunting capacitor to simulate an R-wave pulse at the output of the activating in response to the ventricular pacer signal.

Noise and other electrical interference are filtered in the preferred embodiment of the present invention by means of shunting capacitors to ground across each electrical connection to the converting circuits and activating means. In this manner false activating signals are eliminated, and the pump will be activated at the proper times.

In the preferred embodiment of the present invention, the sensing means includes a bracket which is removably securable to the housing of the pacemaker. Preferably, the bracket has a base portion having an interior surface and opposed side portions projecting from the base portion at a spacing for mounting over the sides of the pacemaker housing. The housing of the pacemaker has a surface in which the optical indicating means is disposed for emission of the optical signals therefrom. The indicating means includes an atrial pace indicator light means and a ventricular pace indicator light means, and the interior surface of the base of the bracket includes two optical sensing electronic devices, preferably optical coupling transistors, mounted therein with their lenses disposed for positioning over the pace light means when the base portion is disposed in covering facing relation on the surface of the pacemaker for sensing of the emitted optical signals. Preferably, the bracket surface is opaque to prevent sensing by the optical coupling transistors of optical signals from optical sources other than the pace light means.

The preferred apparatus includes a means for removably securing the bracket on the housing with the bracket surface in covering relation to the indicating means with the transistor lenses aligned with the indicator light means for sensing of the emitted optical signals. An embodiment of the securing means comprises extensions projecting from the side portions of the bracket over the surface of the pacemaker housing opposite the surface in which the optical indicating means is disposed. The extensions act in securing engagement with the opposite surface to retain the bracket in covering relation on the housing. Another embodimen of the securing means comprises a releasable strap assembly secured to and extending between the side portions opposite the base portion for strapping of the bracket onto the housing.

In the preferred embodiment of the present invention, the bracket has a positioning flange projecting from the interior surface for engagement with the end of the housing extending between the opposed housing surfaces proximal the indicator light means to position the bracket on the housing.

A multiconductor shielded cable preferably extends from the optical coupling transistors to the activating means and is of a sufficient length to accommodate location of the activating means adjacent the pump. The shielded cable prevents the induction of noise and other interference from electrical or electronic equipment in use in the operating room, and in conjunction with the filtering capacitors, helps to provide clean electrical signals simulating the patient's ECG trace for proper timing of counterpulsation by the pump.

BRIEF DESCRIPTION OF THE DRAWINGS

FIG. 3 is an exploded perspective view of the pacemaker, sensing means bracket, and converting means of FIG. 2;

FIG. 4 is a perspective view of one embodiment of the bracket of the apparatus of the present invention;

DETAILED DESCRIPTION OF THE PREFERRED EMBODIMENT

Figure 1:
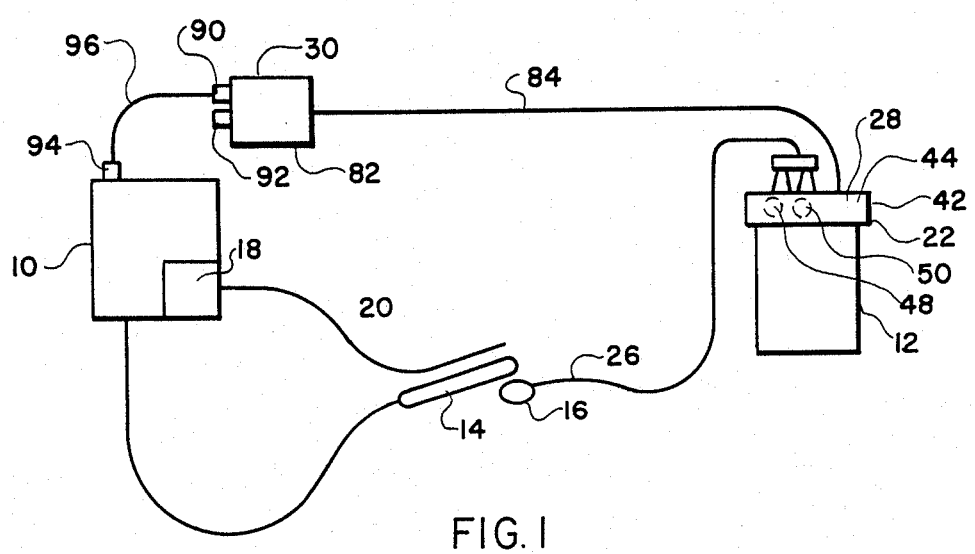
FIG. 1 is a schematic view of a pacemaker, an intra-aortic pump and the pump activating apparatus of the preferred embodiment of the present invention.

Referring now to the accompanying drawings and initially to FIG. 1, the present invention is illustrated for use in activating an intra-aortic balloon pump console, such as the Kontron Model 3000 Intra-aortic Balloon Pump Console indicated at 10 in FIG. 1 on a patient whose heart 16 is externally paced by a pacemaker 12 of the type having an optical indicating means which emits optical signals corresponding to pacer signals generated by the pacemaker 12, such as a Medtronic Model 5330 A-V Sequential Demand Pulse Generator. The present invention is also useful in activating a pulsatile heart-lung bypass pump, such as a Stockert-Shiley Pulsatile bypass pump, of similar equipment requiring precise activation in time with the patient's heart. By way of example, when the surgical procedure calls for a balloon pump 14, it is inserted into the patient's aorta for counterpulsation to assist a weak or failing heart 16 circulate the blood. Conventionally, the balloon pump 14 is activated by the patient's electrocardiogram. An electrocardiogram device 18 is contained within the Kontron Model 3000 Intra-aortic Balloon Pump Console 10; however, the patient's electrocardiogram may be insufficient to trigger the pump and the electrocardiogram leads 20 are susceptible to induced noise and interference from other electrical devices in the operating room, recovery room or intensive care unit which can result in false activation of the pump 10, severely disturbing the counterpulsation-circulatory assist during the period when most needed, as previously discussed. The present invention eliminates these problems associated with counterpulsation of those patients whose hearts 16 are externally paced by a pacemaker 12.

The illustrated apparatus includes an optical sensing means 22 for sensing the optical signals from the optical indicating means indicated generally at 14 in Fig. 3, means for converting 28 the optically sensed signals into electrical signals phased with the pacer signals generated by the pacemaker 12, and means for activating 30 the pump 14, contained within a protective enclosure 82, in response to the electrical signals for operation of the pump 14 in phase with the pacer signals.

The pacemaker 12 is a low voltage battery powered unit while the intra-aortic balloon pump console 10 is powered by 120 volts A.C. Since the electrodes 16 of the pacemaker are electrically connected directly to the patient's heart 16, safety requirements necessitate that the balloon pump console 10 not be electrically connected directly to the pacemaker 12, thereby isolating the patient from potential shock hazard due to shorting of the higher line voltage through the pacemaker 12. The safety of the patient is preserved by the present invention in that signals corresponding to the pacer signals are optically sensed, and the converting of these optically sensed signals to electrical signals and activating the pump 14 in response to the electrical signals are accomplished electrically separate from the pacemaker 12.

Conventional pacemakers 12, such as the Medtronic Model 5330 A-V Sequential Demand Pulse Generator, generally have a rectangular box shaped housing 32 approximately 6" high, 2⅞" wide and 1¾" deep. The housing 32 has a surface 34 containing control knobs 36 and in which the optical indicating means 24 is disposed. As best illustrated in FIG. 3, the optical indicating means 24 includes an atrial pace indicator light means 38 that emits optical signals in response to atrial pacer signals generated by the pacemaker 12 and a ventricular pace indicator light means 40 that emits optical signals in response to ventricular pacer signals generated by the pacemaker 12.

Figure 2:
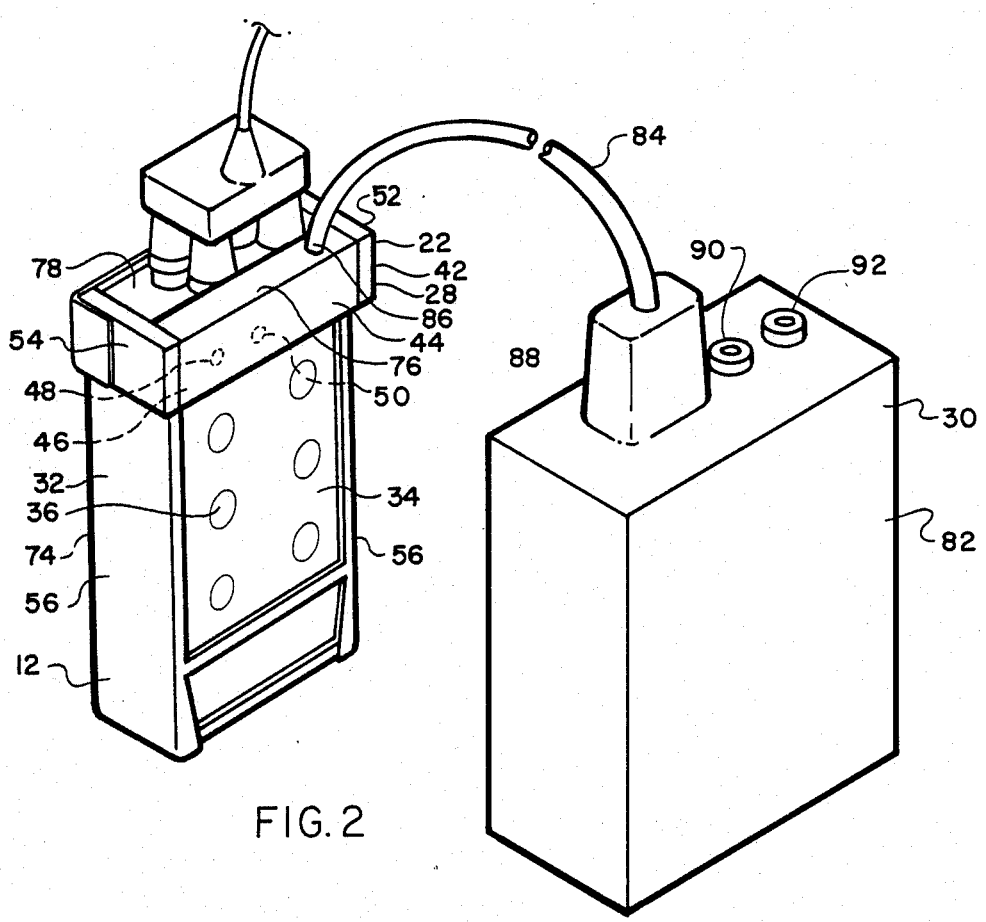
FIG. 2 is a perspective view of the pacemaker, sensing means bracket, and converting means of the apparatus of the embodiment of FIG. 1.

The sensing means 22 includes a bracket 42 which is removably securable to the housing 32 of the pacemaker 12. The bracket 42 has a base portion 44 that includes an interior surface 46. Referring to FIGS. 2 and 3, the interior surface 46 includes two optical coupling transistors 48, 50 mounted therein with their lenses disposed for respective positioning over the atrial pace light means 38 and ventricular pace light means 40 for sensing of the optical signals emitted by each of the pace light means 38, 40 when the base portion 44 is disposed in covering facing relation on the surface 34 of the pacemaker 12, as illustrated in FIG. 2. The bracket 42 has opposed side portions 52, 54 projecting from the base portion 44 at a spacing for mounting over the sides 56 of the pacemaker housing 32.

The bracket 42 of the preferred embodiment of the present invention includes a means 58 for removably securing the bracket 42 on the pacemaker housing 32 with the interior surface 46 of the base portion 44 in covering relation to the atrial and ventricular pace light means 38, 40 with the lenses of the optical coupling transistors 48, 50 aligned with the pace light means 38, 40 for sensing of the emitted optical signals. Referring to FIG. 4, in one embodiment of the bracket 42, the securing means 58 comprises a releasable strap assembly 60 which secures to and extends between the side portions 52, 54 opposite the base portion 46 for strapping the bracket 42 to the pacemaker housing 32, as illustrated in FIG. 2.

Preferably, the strap assembly 60 is a strap 62 adhesively attached or fastened by velcro material at one end 64 to a side portion 52 of the bracket 42 with the opposite end of the strap 66 having a portion of velcro material 68 which will fasten to the mating portion of velcro material 70 attached to the other side portion 54 of the bracket 42.

Figure 5:
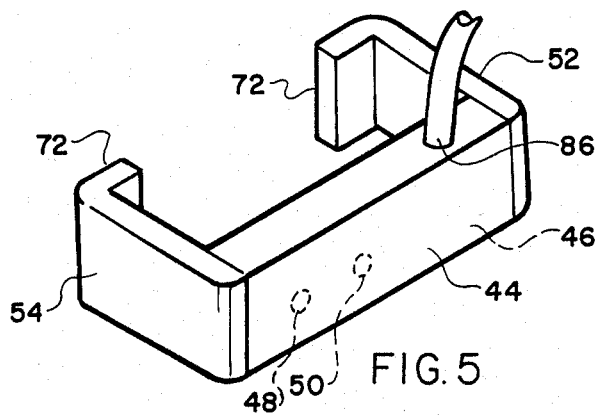
FIG. 5 is a perspective view of another embodiment of the bracket of the apparatus of the present invention.

In another embodiment of the bracket 42, illustrated in FIG. 5, the securing means 58 comprises extensions 72 projecting from the side portions 52, 54 of the bracket 42 essentially perpendicular to the side portions 52, 54 and in opposed spaced facing disposition from the interior surface 46 of the base portion 44. When the bracket 42 is placed in position over the pacemaker housing 32 with the interior surface 46 of the bracket 42 in covering relation with the pace indicator light means 38, 40, the extensions 72 will project over the pacemaker housing surface 74 opposite the surface 34 in which the pace indicator light means 38, 40 are disposed and will securely engage the opposite surface to retain the bracket 42 in place on the housing 32.

Preferably, the bracket surface 46 is opaque, manufactured from black plexiglass or similar material, to prevent sensing by the optical coupling transistors 48, 50 of optical signals from sources other than the atrial and ventricular pace indicator light means 38, 40.

Figures 6, 7:
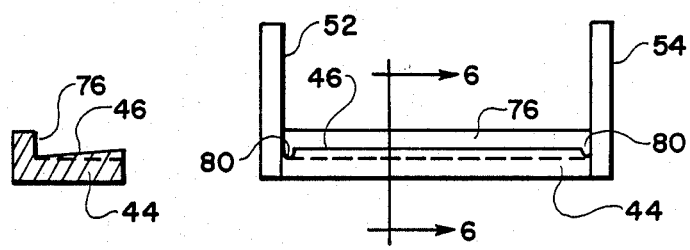
FIG. 6 is an end view of the bracket of FIG. 4 without the strap assembly attached.
FIG. 7 is a cross-section of the bracket of FIG. 6 taken along lines 6—6.

As best illustrated in FIGS. 4, 6 and 7, the bracket 42 has a positioning flange 76 projecting from the interior surface 46 of the base portion 44, and the pacemaker housing 32 has an end 78 extending from the surface 34 of the pacemaker 12 with which the stop flange 76 engages to position the bracket 42 on the pacemaker housing 32, as illustrated in FIG. 2.

The base portion 44 of the bracket 42 may also have grooves 80 where the side portions 52, 54 extend from the base portion 44 to facilitate a tight fit when the bracket 42 is in position on the pacemaker housing 32 to prevent sensing from optical sources other than the pace indicator light means 38, 40. The interior surface 46 of the base portion 44 may also be inclined to more accurately direct the lenses of the optical coupling transistors 48, 50 toward the indicator pace light means 38, 40 to facilitate sensing by the transistors 48, 50.

Figure 8:
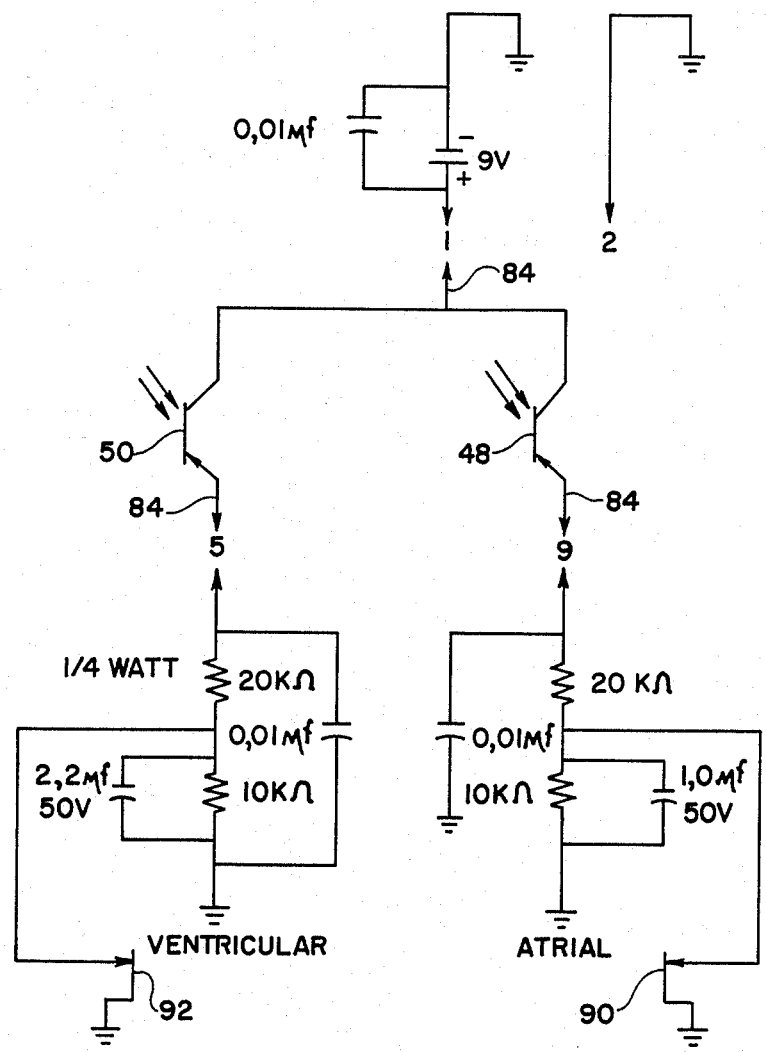
FIG. 8 is a schematic view of the preferred embodiment of the converting circuit of the apparatus of the present invention.

The converting means 28 includes an atrial converting circuit energized in response to optical signals emitted by the atrial pace indicator light means 38 corresponding to the atrial pacer signals generated by the pacemaker 12 and a ventricular converting circuit energized in response to the optical signals emitted by the ventricular pace indicator light means 40 corresponding to the ventricular pacer signals generated by the pacemaker 12. Referring to FIG. 8, the atrial converting circuit includes a 9-volt battery which is contained within the protective enclosure 82 of the activating means 30, the collector electrode of the optical coupling transistor 48, and the emitter electrode of the optical coupling transistor 48. When the atrial pace indicator light means 38 emits an optical signal which is sensed by the optical coupling transistor 48, the transistor 48 will conduct and the circuit will be energized in that a voltage signal derived from the 9-volt battery will be generated at the emitter or output of the transistor 48 in response to the sensed optical signal. In this sense the optical signal sensed is converted to an electrical signal which is phased with the pacer signal generated by the pacemaker 12. Similarly, the ventricular converting circuit includes the same 9-volt battery, the collector electrode of the optical coupling transistor 50, and the emitter electrode of the transistor 50. When the ventricular pace indicator light means 40 emits an optical signal which is sensed by the optical coupling transistor 50, the transistor 50 will conduct, energizing the circuit, and a voltage signal will be generated at the output of the transistor 50.

The 9-volt battery is electrically connected to the collectors of the optical coupling transistors 48, 50 by a multiconductor shielded cable 84. The emitters of the transistors 48, 50 are electrically connected to the activated means 30 via the same cable 84 as illustrated in FIG. 8. The cable 84 is shielded to minimize inductance of noise and interference from other electrical equipment onto the conductors of the cable 84. Preferably, the shielded cable 84 is of sufficient length to locate the outputs of the activating means 30 adjacent the pump console 10 as illustrated in FIG. 1 to further minimize induction of noise and interference.

One end of the cable 84 is molded into the base portion 44 of the bracket 42 and the other end has a 9-pin plug 88 for connecting to a 9-pin jack (not shown) mounted in the surface of the enclosure 82. The plug 88 permits the optical coupling transistors 48, 50 mounted in the bracket 42 to be disconnected from the 9-volt battery and the activating means 30 contained within the protective enclosure 82 to convserve the battery when the apparatus is not in use. The battery is in a sense switched off by disconnecting the plug 88 from the jack mounted in the enclosure 82.

Additionally, the apparatus includes a means for electrically filtering noise and interference that becomes induced upon the signal conductors from the electrical signals carried by the conductors prior to application of the electrical signals by the activating means 30 to the pump console 10 for activation of the pump 14. Referring to FIG. 8, the noise filtering means includes 0.01 microfared capacitors shunting all signal conductors to ground. In this manner, noise and interference from other electrical equipment may be electrically filtered from the electrical signals prior to activating the pump 14 by short circuiting to ground via the capacitors any high frequency energy, such as the interference generated by an electrocautery unit, that may be induced upon the signal conductors of the shielded cable 84.

The activating means 30 includes a means for electrically shaping the waveform of the voltage signals at the outputs of the converting circuits to simulate ECG signals capable of activating the balloon pump 14 in FIG. 1. The output or emitter of the optical coupling transistor 48 which senses optical signals from the atrial light means 38 is electrically connected by the multiconductor cable 84 via pin 9 of the 9-pin plug to the means for shaping the waveform of the voltage signal to simulate an atrial pulse in response to an atrial signal generated by the pacemaker 12. Referring to FIG. 8, the means for shaping the waveform of a voltage signal generated by the transistor 48 in response to an optical signal emitted by the atrial light means 38 to simulate an atrial pulse for proper activation of the pump 14 includes a circuit having a 20K-ohm resistor in series with a 10K-ohm resistor to define a voltage divider with a 1.0 microfared capacitor shunting the 10K-ohm resistor to widen the pulse to simulate an atrial pulse and to insure proper activation of the pump 14. This pulse also shuts off the R-wave detection circuit in the pump console 10 at the time that the atrial pacer pulse is present on the ECG complex. Similarly, the output or emitter of the optical coupling transistor 50 which senses optical signals from the ventricular light means 40 is electrically connected by the multiconductor cable 84 via pin 5 of the 9-pin plug 88 to the means for shaping the waveform of the voltage signal to simulate an R-wave pulse in response to a ventricular pacer signal generated by the pacemaker 12. This means for shaping the voltage signal to simulate an R-wave includes a circuit having a 20K-ohm resistor in series with a 10K-ohm resistor to define a voltage divider with a 2.2 microfared capacitor shunting the 10K-ohm resistor to shape the R-wave pulse in response to a ventricular pulse generated by the pacemaker 21.

Once the voltage signals are shaped into the proper waveform to activate the pump, the activating means 30 applies the voltage signals to the pump console 10 for activation of the pump 14. The activating means 30 includes a jack 90 conected at the output of the atrial waveshaping circuit and mounted in the surface of the enclosure 82, and another jack 92 connected at the output of the ventricular waveshaping circuit and mounted in the surface of the enclosure 82 as illustrated in FIGS. 2, 3 and 8. The pump is then activated by electrically connecting either the ventricular output jack 92 or the atrial output jack to the monitor jack 94 of the pump console 10 with a two conductor shielded cable 96 terminated at each end with a three conductor plug (not shown). This cable 96 is shielded and preferably of relatively short length compared to that of the multiconductor shielded cable 84, preferably no more than three feet, to further minimize inductance of noise and interference on the conductors of the cable 96 and to prevent false activation of the pump 14.

Although the preferred embodiment of the present invention discloses the use of optical coupling transistors 48, 50 to sense to optical signal and convert these signals to electrical signals, those persons skilled in the art will readily recognize that photodiodes or similar optically responsive electronic devices could equally be employed.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention.

The foregoing disclosure is not intended or to be construed to limit the present invention or otherwise to exclude any such other embodiments, adaptations, variations, modifications and equivalent arrangement, the present invention being limited only by the claims appended hereto and the equivalents thereof.

We claim:

1. A method for activating a pulsatile heart-lung bypass pump, intra-aortic balloon pump or the like on a patient whose heart is externally paced by a pacemaker of the type having an optical indicating means which emits optical signals corresponding to pacer signals generated by said pacemaker, said method comprising:
    optically sensing said optical signal,
    converting said optical signal sensing into electrical signals, phased with said pacer signals and
    activating said pump in response to said electrical signals for operation of said pump in phase with said pacer signals.

2. A method according to claim 1 wherein said pacemaker includes a low voltage power source and said pump includes a higher voltage power source of potential hazard to said patient, said method characterized further in that said sensing, converting, and activating are accomplished electrically separate from said pacemaker, thereby isolating said patient from potential shorting of said hazardous higher voltage through said pacemaker.

3. A method according to claim 1 wherein one of said optical signals corresponds to atrial pacer signals generated by said pacemaker and another of said optical signals corresponds to ventricular pacer signals generated by said pacemaker, said method characterized further in that said optical sensing senses one of said optical signals, with said activating thereby being responsive to the electrical signals converted from said one of said optical signals.

4. A method according to claim 3 and characterized further in that said converting includes energizing an atrial converting circuit in response to said optical signals corresponding to said atrial pacer signals and energizing a ventricular converting circuit in response to said optical signals corresponding to said ventricular pacer signals.

5. A method according to claim 4 and characterized further in that said circuits generate voltage signals at the output of said circuits, and said activating applies said voltage signals of one of said circuits to said pump.

6. A method according to claim 1 and characterized further in that said method includes electrically filtering noise from said electrical signals prior to activating said pump.

7. A method according to claim 5 and characterized further in that said activating includes electrically shaping the waveform of said voltage signals to simulate ECG signals capable of activating said pump.

8. A method according to claim 7 and characterized further in that said electrically shaping the waveform of said voltage signals includes simulating an atrial pulse in response to said atrial pacer signal and simulating an R-wave pulse in response to said ventricular pacer signal.

9. A method according to claim 1 and characterized further in that said converting includes energizing an electrical circuit in response to said optical signal sensing and generating voltage signals in said circuit at the output thereof, and said activating includes electrically shaping the waveforms of said voltage signals to simulate ECG signals capable of activating said pump and applying said electrically shaped voltage signals to said pump.

10. A method according to claim 9 and characterized further in that said method includes electrically filtering noise from said electrical signals prior to activating said pump.

11. An apparatus for activating a pulsatile heart-lung bypass pump, intra-aortic balloon pump or the like on a patient whose heart is externally paced by a pacemaker of the type having an optical indicating means which emits optical signals corresponding to pacer signals generated by said pacemaker, said apparatus comprising:
    means for optically sensing said optical signals,
    means for converting said optical signal sensing into electrical signals phased with said pacer signals, and
    means for activating said pump in response to said electrical signals for operation of said pump in phase with said pacer signals.

12. An apparatus according to claim 11 wherein said pacemaker includes a low voltage power source and said pump includes a higher voltage power source of potential hazard to said patient, said apparatus characterized further in that said sensing means, converting means, and activating means are electrically separate from said pacemaker, thereby isolating said patient from potential shorting of said hazardous higher voltage through said pacemaker.

13. An apparatus according to claim 11 wherein one of said optical signals corresponds to atrial pacer signals generated by said pacemaker and another of said optical signals corresponds to ventricular pacer signals generated by said pacemaker, said apparatus being characterized further in that said optical sensing means senses one of said optical signals, with said activating means thereby being responsive to the electrical signals converted from said one of said optical signals.

14. An apparatus according to claim 13 and characterized further in that said converting means includes an atrial converting circuit energized in response to said optical signals corresponding to said atrial pacer signals and a ventricular converting circuit energized in response to said optical signals corresponding to said ventricular pacer signals.

15. An apparatus according to claim 14 and characterized further in that said circuits generate voltage signals at the output of said circuits, and said activating means applies said voltage signals of one of said circuits to said pump.

16. An apparatus according to claim 15 and characterized further in that said activating means includes means for electrically shaping the waveform of said voltage signals at the output of said activating means to simulate ECG signals capable of activating said pump.

17. An apparatus according to claim 16 and characterized further in that said means for electrically shaping the waveform of said voltage signals includes a resistive voltage divider with capacitance shunting said divider to simulate an atrial pulse in response to said atrial pacer signal and another resistive voltage divider with shunting capacitance to simulate an R-wave pulse in response to said ventricular pacer signal.

18. An apparatus according to claim 11 and characterized further in that said apparatus includes means for electrically filtering noise from said electrical signals prior to application of said electrical signals to said pump by said activating means.

19. An apparatus according to claim 11 and characterized further in that said converting means includes an eletrical circuit energized in response to said optical signal sensing for generating voltage signals in said circuit at the output thereof, and said activating means includes means for electrically shaping the waveforms of said voltage signals to simulate ECG signals capable of activating said pump and applying said electrically shaped voltage signals to said pump.

20. An apparatus according to claim 19 and characterized further in that said apparatus includes means for electrically filtering noise from said electrical signals prior to application of said electrical signals to said pump by said activating means.

21. An apparatus according to claim 20 and characterized further in that said means for electrically filtering noise includes shunting capacitors to ground across each electrical connection to said circuit and said means for electrically filtering noise.

22. An apparatus according to claim 11 wherein said pacemaker has a housing with a surface in which said optical indicating means is disposed for emission of said optical signals therefrom, said apparatus characterized further in that said sensing means includes a bracket removably securable to said housing, said bracket having an interior surface and having at least one optical sensing electronic device mounted therein with said device being disposed in said bracket surface and means for removably securing said bracket on said housing with said bracket surface in covering relation to said indicating means with said device aligned with said indicating means for sensing of said emitted optical signals.

23. An apparatus according to claim 22 wherein said housing has opposed sides extending from said surface, said apparatus characterized further in that said bracket has a base portion that includes said interior surface and opposed side portions projecting from said base portion at a spacing for mounting over said housing sides.

24. An apparatus according to claim 23 wherein said housing has a surface opposite said surface in which said optical indicating means is disposed, said apparatus characterized further in that said securing means comprises extensions projecting from said side portions of said bracket over said opposite surface of said housing in securing engagement with said opposite surface.

25. An apparatus according to claim 23 and characterized further in that said securing means comprises a releasable strap assembly secured to and extending between said side portions opposite said base portion for strapping of said bracket on said housing.

26. An apparatus according to claim 22 and characterized further in that said bracket surface is opaque to prevent sensing by said optical sensing electronic device of optical signals from optical sources other than said optical indicating means.

27. An apparatus according to claim 22 and characterized further in that said indicating means includes an atrial pace indicator light means and a ventricular pace indicator light means and said interior surface of said bracket includes two optical sensing electronic devices mounted therein disposed for positioning over said pace light means when said base portion is disposed in covering facing relation on said surface of said pacemaker.

28. An apparatus according to claim 27 and characterized further in that said bracket surface is opaque to prevent sensing by said optical sensing electronic devices of optical signals from optical sources other than said pace light means.

29. An apparatus according to claim 22 wherein said housing has an end extending from said surface, said apparatus characterized further in that said bracket has a positioning flange projecting from said surface for engagement with said housing end to position said bracket on said housing.

30. An apparatus according to claim 22 and characterized further by a multi-conductor shielded cable extending from said optical coupling transistors a length sufficient to accommodate location of said activating means adjacent said pump.

* * * * *

UNITED STATES PATENT AND TRADEMARK OFFICE
CERTIFICATE OF CORRECTION

PATENT NO. : 4,827,906

DATED : May 9, 1989

INVENTOR(S) : Francis Robicsek and Richard P. Morency

It is certified that error appears in the above-identified patent and that said Letters Patent is hereby corrected as shown below: TITLE PAGE:

Abstract, Line 14, after "transistors" add -- mounted --.

Column 1, Line 7, delete "field" and insert therefor -- filed --.

Column 1, Line 7, after "1987" add -- now --.

Column 1, Line 53, delete "10" (boldface type) and insert therefor -- 10 -- (non-boldface type).

Column 2, Line 28, delete "emit" and insert therefor -- emits --.

Column 4, Line 5, delete "embodimen" and insert therefor -- embodiment --.

Column 4, Line 63, delete "of" and insert therefor --or--.

Column 8, Line 26, delete "21" and insert therefor -- 12 --.

Column 8, Line 31, delete "conected" and insert therefor -- connected --.

Column 8, Line 49, delete "to" (second occurrence thereof) and insert therefor -- the --.

Signed and Sealed this

Sixteenth Day of June, 1992

Attest:

DOUGLAS B. COMER

*Attesting Officer*　　　*Acting Commissioner of Patents and Trademarks*